United States Patent
Zeng (12)

(10) Patent No.: US 6,440,949 B1
(45) Date of Patent: Aug. 27, 2002

(54) METHOD FOR PROMOTING THE GROWTH OF GRAM-POSITIVE BACILLI AND INCREASING THE ACIDITY IN VAGINA

(75) Inventor: Zhongming Zeng, Shenzhen (CN)

(73) Assignee: Shanghai Jiao Da Onlly Co., Ltd., Shanghai (CN)

(*) Notice: Subject to any disclaimer, the term of this patent is extended or adjusted under 35 U.S.C. 154(b) by 0 days.

(21) Appl. No.: 09/578,177

(22) Filed: May 24, 2000

Related U.S. Application Data

(63) Continuation of application No. PCT/CN98/00278, filed on Nov. 24, 1998.

(30) Foreign Application Priority Data

Nov. 24, 1997 (CN) ................................................ 971227

(51) Int. Cl.$^7$ ..................... A61K 31/415; A61K 31/425; A61K 31/495; A61K 31/715
(52) U.S. Cl. ....................... 514/58; 514/60; 514/252.14; 514/370; 514/383; 514/398
(58) Field of Search ....................... 514/58, 60, 252.14, 514/370, 383, 398

(56) References Cited

U.S. PATENT DOCUMENTS

| | | | |
|---|---|---|---|
| 3,860,707 A | | 1/1975 | Wootton ..................... 424/180 |
| 4,837,154 A | * | 6/1989 | Spiegel ..................... 435/253.6 |
| 5,211,971 A | * | 5/1993 | Van Dijk et al. ............. 426/18 |
| 5,292,532 A | * | 3/1994 | Bombart ..................... 424/405 |
| 5,518,733 A | | 5/1996 | Lamothe et al. ............ 424/430 |
| 5,573,765 A | * | 11/1996 | Reinhard et al. ........ 424/93.45 |

FOREIGN PATENT DOCUMENTS

| | | |
|---|---|---|
| CN | 1104502 A | 5/1995 |
| EP | 0 257 007 A1 | 2/1988 |
| GB | 2 112 285 A | 7/1983 |
| WO | WO 94/02148 | 2/1994 |
| WO | WO 94/03502 | 2/1994 |

OTHER PUBLICATIONS

Merck Index, 10th edition, 1983, entry No. 8650.*
Caplus abstract of CN 1099615, 1995.*
Germain, Marc, et al., "Genital Flora in Pregnancy and Its Association With Intrauterine Growth Retardation"; *J. Clin. Microbiol*; vol. 32, No. 9; pp. 2162–2168 (Sep. 1994).
McDonald, H.M., et al.; "Vaginal Infection and Preterm Labour"; *Br. J. Obstet Gynaecol*; vol. 98, No. 5; pp. 427–435 (May 1991).
Thomason, Jessica L.; "Bacterial Vaginosis: Current Review With Indications for Asymptomatic Therapy"; Am. J. Obstet Gynecol; vol. 165, No. 4, Part 2; pp. 1210–1217 (1991).
Hillier, Sharon, L.; "Efficacy of Intravaginal 0.75% Metronidazole Gel for the Treatment of Bacterial Vaginoisis"; *Obstet–Gynecol.*; vol. 81, No. 6; pp. 963–967 (Jun. 1993).
Hallén, Anders, MD., et al.; "Treatment of Bacterial Vaginois With Lactobacilli"; *Sex–Transm–Dis.*; vol. 19, No. 3; pp. 146–148 (May–Jun. 1992).
Hughes, Viki, L.; "Microbiologic Chracteristics of Lactobacillus Products Used for Colonization of the Vagina"; *Obstetrics & Gynecology*; vol. 75, No. 2; pp. 244–248 (Feb. 1990).
Eschenbach, David, A.; "Bacterial Vaginosis and Anaerobes in Obstetric–Gynecologic Infection"; *Clinical Infectious Diseases*; vol. 16; Supp. 4; pp. S282–S287 (1993).

* cited by examiner

*Primary Examiner*—Kathleen K. Fonda
*Assistant Examiner*—Leigh C. Maier
(74) *Attorney, Agent, or Firm*—Darby & Darby

(57) ABSTRACT

The present invention relates to a pharmaceutical formulation for stimulating the growth of gram-positive bacilli and increasing the acidity in vagina in which comprises sugar(s), to the use of certain sugar(s), in preparing the pharmaceutical formulation for stimulating the growth of gram-positive bacilli and increasing the acidity in vagina, in particular to a method for stimulating the growth of gram-positive bacilli and increasing the acidity in vagina, treating the reduction of gram-positive bacilli and the lowness of acidity in vagina as well as the vaginitis and the disturbance of vaginal bacterioflora accompanying the reduction of gram-positive bacilli, especially bacterial vaginal disease.

8 Claims, No Drawings

METHOD FOR PROMOTING THE GROWTH OF GRAM-POSITIVE BACILLI AND INCREASING THE ACIDITY IN VAGINA

This is a continuation of international application Ser. No. PCT/CN98/00278, filed Nov. 24, 1998.

FIELD OF THE INVENTION

This invention relates to pharmaceutical compositions containing saccharides as active ingredients for promoting the growth of Gram-positive bacilli and increasing the acidity in the vagina, to the use of particular saccharides in the preparation of compositions for promoting the growth of Gram-positive bacilli and increasing the acidity in the vagina, and especially to a method of promoting the growth of Gram-positive bacilli and increasing the acidity in the vagina, treating decreased levels of Gram-positive bacilli and decreased levels of acidity in the vagina, treating vaginitis and disturbances of the vaginal bacterial flora accompanying the reduction of Gram-positive bacilli, especially bacterial vaginosis.

BACKGROUND OF THE INVENTION

High acidity in female vagina is one important anti-infective mechanism of the vagina and is of great significance for vaginal health. Lactobacilli and other Gram-positive bacilli that can produce and resist acids serve an important role in maintaining the normal acidity in the vagina by keeping the vaginal pH value in the range from 4.0 to 4.6. They are the physiological bacterial flora of vagina, whereas Gram-negative bacilli, Gram-negative cocci, and Gram-positive cocci are relatively less abundant in the healthy vagina.

When the Gram-positive bacilli are reduced or disappear in vagina, vaginal pH value rises and disturbance of vaginal bacterial flora results from abnormal increases of Gram-negative bacilli, Gram-positive cocci and Gram-negative cocci, which can cause harm to the human body and lead to a range of diseases. The most typical condition resulting from altered vaginal flora is bacterial vaginosis (BV). BV is characterized by the reduction or even disappearance of Lactobacillus and other Gram-positive bacilli in the vagina, accompanied by decreased acidity (pH value>4.6) in the vagina, and abnormal increases of such bacteria as Gram-negative bacilli including Gardnerella, Bacteroides and motile-curved bacilli; Gram-negative cocci such as Veillonella; and Gram-positive cocci such as Streptococcus. Such changes in the bacterial flora can cause vaginal secretions to exhibit an unpleasant odor, and may be associated with pruritus of vulva, and symptoms. In addition, BV may also be related to IUGR [1], PTL, PROM [2], abortion, and obstetric infections such as chorio-amnionitis, puerperal endometritis, vaginal wall phlegmon after hysterectomy, female upper genital tract infection (salpingitis), and urinary infection, etc. [3]. A high rate of morbidity is associated with vaginal bacterial flora disturbance. According to one report, about 45% or more vaginitis cases result from disturbance of vaginal bacterial flora [3], and 4–15% of American female students in universities suffer from bacterial vaginosis [4], which has led to serious compromise to health and quality of life.

There are few options for treatment of reduced Gram-positive bacilli colonization, decreased vaginal acidity, and related disturbances of vaginal bacterial flora, vaginitis, and bacterial vaginosis. Therapeutic options currently include:
1) Antibacterial drugs which are used to suppress the growth of Gram-negative bacilli and other abnormal bacteria. These most commonly include clindamycin and metronidazole [5–6]. These drugs suppress the bacteria that are abnormally increased in the vagina but may also affect the Gram-positive bacilli. After administration of these drugs, the Gram-positive bacilli (lactobacilli) can not be restored very well, and it is very difficult to lower the pH value in the vagina to normal level.
2) Lactic acid-containing pharmaceutical compositions. Vaginal secretions from patients suffering from bacterial vaginosis have elevated pH values. Swedish researchers used lactic acid gel for the improvement and recovery of the low-acidity conditions in vagina, and reported that this treatment can restore the Gram-positive bacilli (lactobacilli) in the vaginas of some of the patients [7]. But the study also showed that the lactic acid pharmaceutical preparation is less effective than the antibacterial drugs [8].
Lactobacillus preparations. Most of the Gram-positive bacilli in vagina are lactobacillus. If there is disturbance of vaginal bacterial flora, the lactobacilli will be reduced or disappear, and Gram-negative bacilli, Gram-negative, and Gram-positive cocci, will increase. The Gram-positive bacilli in the vagina of some patients can be restored by directly adding lactobacilli in the vagina [9]. However, stable colonization is generally not achieved. Moreover, it is difficult to maintain viability of the lactobacillus preparations during storage, with viable counts in such preparations decreasing during storage, compromising their useful shelf life [10].

The international Patent Application W094/02148 discloses a pharmaceutical compositions for treating vulvitis and vulvovaginitis, and indicates that such compositions can promote restoration of vaginal epithelium tissues while alleviating the symptoms. Its preferred compositions comprises 7 to 8 active substances. Some preferred compositions may contain 3.0–15.0% (by weight/volume) lactose or glucose. As mentioned in page 5 lines 8–10 of the published specification, the lactose or glucose contained in these compositions is used as carbon source. But this application does not mention that saccharides can be used solely as the effective component for treating vulvitis and vulvovaginitis, and nor does it disclose explicitly or implicitly that the disclosed compositions can stimulate the growth of Gram-positive bacilli in vagina. Furthermore, it does not indicate that any other kinds of sugar can be used as active components of a composition for treating related vaginal diseases. Besides, as mentioned in page 5 lines 17–18 of the specification, this application emphasizes that it is important for the pH value of the compositions be between 2 and 3.5.

The U.S. Pat. No. 3,860,707 teaches a method for treating trichomonal vaginitis and monilial vaginitis. This method comprises administering lactulose into the vagina. This patent also indicates that lactulose can be administered after being mixed with some carriers such as glucose, lactose and galactose, wherein lactulose is required to have a concentration as high as 50%, and the mixture also contains 5% lactose, 8% galactose as carriers, as mentioned in column 1 lines 51–55 and column 5 lines 1–5 of the patent specification. The quantity of lactulose is 4–10 grams administered with each dose which is taken once or twice daily, as shown in Column 4 Lines 63–66 of the specification. But this patent does not describe the treatment effectiveness on bacterial vaginosis or other vaginal diseases different from monilial vaginitis, nor does it suggest that the lactulose of low or medium concentration (2.5–17%) and small dosage (daily total amount 0.24–2.1 grams) would be able to stimulate the growth of Gram-positive bacillus and increase the acidity of the vagina. Furthermore, it fails to indicate whether any saccharide other than lactulose has treatment effects.

European Patent Application EP-A-0257007 discloses a pharmaceutical composition containing lactic acid and buffering substances and substrate to support growth of lactobacillus, which can be used to improve microenvironment in vagina and suppress the growth of harmful bacteria in the vagina, so as to facilitate the growth of lactobacilli. This patent application discloses that glycogen or lactose can be used as the said substrate. But as mentioned in Column 6 Line 10–14 of the specification, the main ingredient of this composition is lactic acid. The lactic acid and the glycogen and/or lactose are incorporated in a ratio by weight of from 20:1 down to 500:1, and the content of glycogen and/or lactose is only 0.1–0.166%(W/V). It also stresses that the pH value of the pharmaceutical composition should be adjusted to 3.5 to 4.0, which is very important. The in vitro experimental results disclosed in this application show that this composition can effectively and selectively kill pathogenic bacteria, and lactobacilli can survive in this composition for a longer time than the pathogenic microorganisms. But no test in vitro or vivo shows that this composition can stimulate the growth of lactobacilli or produce acids. Nor does this application mention the treatment effect of glycogen or lactose or any other saccharides when they are used separately as active ingredients.

GB2112285A discloses a lotion composition for cleaning the vagina. It is a buffering liquid comprising acetic acid or lactic acid plus sodium acetate with a pH value of 5.71 to 6.2 as shown in the examples. It also contains nutrients to support the growth of lactobacillus [1–2% (W/V) glucose and unsaturated fatty acid]. It also generally mentions inclusion of mono- and/or disaccharides. The main therapeutic mechanism of this composition is that the buffering lotion comprising acetic acid or lactic acid plus sodium acetate can selectively suppress pathogens and not suppress lactobacilli. As shown in claims 2 and 3 and the in vitro test data of this application, this lotion can effectively suppress many kinds of pathogens, and lactobacilli survive in this composition for a longer time. No data from test in vitro or vivo indicates that this lotion has an activity of promoting the growth of lactobacilli and producing acid, nor does it indicate the treatment effect of glucose or any other sugar when used separately as active ingredients. This application teaches that lactobacilli regulate pH value in vagina to about 5.8, as shown in Page 1 Lines 20–23 of the specification, which is strongly contradicted by most knowledgeable investigators.

The above-mentioned pharmaceutical compositions disclosed in patent applications EP-A-0257007 and GB2112285A which contain lactic acid, acetic acid and other selective inhibitors as main active ingredients have strong suppressive action on pathogens but no explicit suppressive action on lactobacilli, although they may indirectly facilitate the growth of vaginal lactobacilli. These compositions themselves, however, cannot directly promote significant growth of lactobacilli, and only regulate vaginal acidity for a short time. Therefore, it remains very difficult to restore the physiological conditions dominated by the Gram-positive bacillus-flora and to restore the vaginal acidity to its normal value.

The object of the present invention is to provide a composition for promoting the growth of Gram-positive bacilli and the production of acids, and thus increase the acidity in the vagina. Another object of the present invention is to provide a method by using such composition for reversing the reduction of Gram-positive bacilli, lack of vaginal acidity and treating related vaginal diseases.

In order to seek a composition which is effective in promoting the growth of Gram-positive bacilli, producing acid, and enhancing the acidity in the vagina, the inventor has conducted an extensive study, performed tests by using various pharmaceutical compositions known in the prior art, and has not found any compositions promoting the growth of Gram-positive bacilli among the existing compositions. After repeated tests and intensive study, the inventor has found very surprisingly that most nature-occurring hexoses and oligosaccharides and particular polysacharides have an effect of promoting the growth of Gram-positive bacilli and producing acids if they are presented in a concentration and at a pH value in specific ranges. Combined in vitro culturing experiments show that most of the tested saccharides can stimulate the growth of Gram-positive bacilli by a varying degree, increasing their numbers significantly. To our surprise, although pH values above 4.6 in vagina are considered unphysiologic, and most of state-of-the-art technologies stress that the pharmaceutical compositions used in vagina must have a pH value equal to 4.0 or below, the inventor has discovered that, if they have pH value between 4.1 and 7.2, and especially above pH 5.0, the tested saccharides can stimulate the growth of Gram-positive bacilli of women vagina and the production of acid, and are able to decrease the pH value in vagina to less than 4.6. However, if they have pH values of 4.0 or less, they do not exert significant growth-promoting effects on Gram-positive bacilli nor upon acid production and the pH of the vagina can rarely be reduced to below 4.6. Based on the above discoveries and further study, the inventor has completed the present invention.

SUMMARY OF THE INVENTION

The present invention provides a water-based pharmaceutical composition for promoting the growth of Gram-positive bacilli and increasing the acidity in the vagina comprising, based on the volume of the composition, 2.5% to 17% (W/V) of one or more saccharides selected from the group consisted of hexoses such as glucose, fructose, galactose and mannose; oligosaccharides such as lactose, lactulose, mycose, cellobiose, melibiose, melitose, malto-oligosaccharide, iso-malto-oligosaccharide and oligo-fructose; and polysaccharides such as dextrin, starch and glycogen, at pH-value of 4.1–7.2 adjusted with pharmaceutically acceptable acid or alkali, optionally a pharmaceutically acceptable viscous base, and optionally an effective amount of anti-fungal and/or an anti-bacterial agents.

The invention also provides a use of one or more saccharides selected from the following group as active ingredients in the preparation of pharmaceutical compositions for promoting the growth of Gram-positive bacilli and increasing the acidity in the vagina: hexose such as glucose, fructose, galactose and mannose; oligosaccharides such as lactose, lactulose, mycose, cellobiose, melibiose, melitose, malto-oligosaccharide, iso-malto-oligosaccharide and oligo-fructose; and polysaccharides such as dextrin, starch and glycogen.

The invention also relates to a method for promoting the growth of Gram-positive bacilli and increasing the acidity in the vagina, comprising administering to the subject in need of such treatment a therapeutically effective amount of the pharmaceutical composition according to the present invention.

The above-mentioned pharmaceutical composition, use and method of treatment according to the invention are useful for the reversal of the reduced numbers of vaginal Gram-positive bacilli, decreased vaginal acidity, as well as for treating vaginitis and the disturbance of vaginal bacterial flora accompanied with the reduction in numbers of Gram-positive bacilli, especially bacterial vaginosis.

DETAILED DESCRIPTION OF THE INVENTION

As mentioned above, this invention relates to water-based pharmaceutical compositions with pH values between 4.1 and 7.2 intended to promote the growth of Gram-positive bacilli and enhance vaginal acidity, and which contains 2.5–17% (W/V) of one or more of such saccharides as defined above.

The compositions according to the present invention may contain one or a mixture of two or several of such saccharides as defined above. Any hexose used in the invention is of D-type. Starch used in the invention may be amylose or amylopectin. The preferred saccharides are lactulose, cellobiose, malto-oligosaccharide, mycose or a mixture therof.

According to this invention, the pharmaceutical composition contains a total content of 2.5–17% (W/V) of saccharides, especially 2.5–16% (W/V), preferably 8–14% (W/V), more preferably 10–13% (W/V), and most preferably 10–12% (W/V). However, the content of the hexose should be less than 7.2%(W/V). The maximum content of hexoses mixed with disaccharides should be less than [0.42×( 17-disaccharides content ) % (W/V)].

The weight/volume content (W/V) mentioned in the context of this application refers to the grams of the specified component in 100 milliliters of the composition.

The compositions formulated according to the preferred contents of saccharides are useful for treating the patients with any vaginal illness states, especially with severe illness (with pH value of vaginal secretion greater than 5.0, and when the vaginal Gram smear proves that there are few or no Gram-positive bacilli). The compositions with a content of saccharides below 8% (W/V) are applicable to the patients suffering from mild diseases (with a vaginal pH value of greater than 4.6, and the vaginal Gram smear proves that there are Gram-positive bacilli, but in which the Gram positive bacilli are fewer in number than the Gram-negative bacilli, Gram-negative cocci, or Gram-positive cocci).

The pH value of the pharmaceutical compositions of this invention is between 4.1 and 7.2, with the optimum pH value between 4.5 and 6.5. The pH value of these compositions can be adjusted by adding any pharmaceutically acceptable acid or alkali, of which the preferred choices are acetic acid, lactic acid, or sodium hydroxide. The nature and concentration of such acid or alkali can be readily determined by a person skilled in the art.

According to this invention, the composition may contain a viscous base. One example of such base is Xanthan Gum with concentration of 1.0–2.2% (W/V), and preferably of 1.4–2.0% (W/V). Xanthan Gum is able to keep the sugar in uniform contact with vaginal mucosa and retain the product within the vaginal vault for a long time due to its high adherence and stability against changes of temperature and pH values, thus permit the compositions to promote the growth of Gram-positive bacilli and increasing the production of acid in vagina.

The composition can also be formulated into gel form or ointment with other suitable viscous carrier bases, auxiliaries well known to a person skilled in the art.

According to this invention, the composition also may not contain viscous base, it may be administered by means of intravaginal tampon saturated with the liquid composition. The intravaginal tampon may be composed of cotton ball, gauze ball, ribbon gauze, etc. In this embodiment, the composition according to the present invention can also stimulate the growth of Gram-positive bacilli and increase the acidity in the vagina. The preferred use of the composition of this invention does requires that the composition of the invention stay in the vagina for some time before it can stimulate the growth of Gram-positive bacilli and produce vaginal acidity in the vagina. Therefore as a lotion without a viscous base, the composition can not exhibit its therapeutic effect very well.

The saccharide(s) is/are the essential basic active components of the composition of the invention, and can fulfill the object of this invention when used with suitable pharmaceutically acceptable carriers. But these saccharides can produce a better treatment effect if it is combined with minor amount of amino-acid, vitamin or other similar substances, or yeast extract rich in amino-acids and vitamins. The vaginal secretion naturally contains sufficient amino-acids and vitamins. Such amino-acids or vitamins are not available in conventional in vitro experiments and should be added when in vitro experiments are carried out for the composition of the invention.

The composition of the invention may also contain one or more anti-fungal agents in an effective amount, and may be used for the control of possible increased fungal growth. The anti-fungal agents may include but are not limited to ketoconazole, terconazole, itraconazole and fluconazole.

The composition of the invention may also contain one or more anti-bacterial agents that can suppress or kill Gram-negative bacteria but exert no effect or only exert slight effect on Gram-positive bacilli. In this embodiment, the composition of the invention may have an increased efficacy for treating vaginal infection or inflammation. Such anti-bacterial agents may include, but are not limited to polymyxin, metronidazole or aztreonam.

The composition of the invention can be prepared according to the processes known to those skilled in the art.

If the saccharides used only include hexose, oligosaccharide, dextin or mixture thereof, such saccharides should be mixed with viscous auxiliary substances homogeneously, and then distilled water is added into the mixture, which are then stirred to dissolve the saccharide and swell the viscous auxiliary substances until a homogeneous viscous gel is formed. If starch is included, it is sufficient to heat directly the mixture of saccharides and water to form a paste. In the latter case, viscous auxiliary substances may be added or not. For adjusting the pH to a predetermined value, lactic acid or sodium hydroxide solution is added prior to sterilization treatment. Alternatively, sterilization treatment is performed first, followed by adjustment of pH. For sterilization, intermittent sterilization may be used, with the detailed steps described as follows: sterilizing at 80° C. for 30 minutes, keeping at 36° C. for 8–12 hours, sterilizing at 80° C. for 30 minutes, keeping at 36° C. for 8–12 hours and finally sterilizing at 80° C. for 30 minutes. Alternatively, a high-pressure sterilization may be performed for 15–20 minutes at 116° C. A solution of saccharides may also be sterilized by filtering the solution. Then the sterilized saccharide solution may be added to an viscous base in the form of gel that has been sterilized at high pressure.

The composition of the invention also may be made into a solution by dissolving the saccharides in water. The solution can be administered to a patient by means of an intravaginal tampon soaked in it.

The composition of this invention uses sugar substances as active ingredients, and has good stability during storage, but preferably it is stored under refrigeration or in cool place. The near neutral pH value of the composition is also helpful in stabilizing the sugar components.

The present invention also relates to the use of one or more of such saccharides as defined above as active ingredients in the preparation of a medicament for promoting the growth of Gram-positive bacilli and increasing the acidity in the vagina. This invention uses D-type hexose, either amylose or amylopectin.

The medicament prepared according to the use of the invention can be used for promoting the growth of Gram-positive bacilli and increasing the acidity in the vagina, and reversing decreased numbers of Gram-positive bacilli, diminished vaginal acidity (pH value above 4.6) as well as treating vaginitis and the disturbance of vaginal bacterial flora accompanied with the reduction of Gram-positive bacilli, especially bacterial vaginosis.

The experiments in vitro and in vivo have proven that the composition of the invention can strongly stimulate the growth of Gram-positive bacilli and increase the acidity in the vagina, and can be used for the reversal of the reduction of Gram-positive bacilli, diminished vaginal acidity and treatment of vaginitis and the disturbance of vaginal bacterial flora accompanied with reduction of Gram-positive bacilli, especially bacterial vaginosis.

Therefore, this invention also relates to a method for promoting the growth of Gram-positive bacilli and increasing vaginal acidity, reversing the reduction of Gram-positive bacilli, increasing vaginal acidity and treatment of vaginitis and the disturbance of vaginal bacterial flora that accompanied with reduction of Gram-positive bacilli, especially bacterial vaginosis, wherein the subject in need of such treatment is given a medically-effective amount of the pharmaceutical composition according to the invention.

The administration method of the composition is to administer the composition locally inside the vagina. The composition of the invention containing a tissue viscous base or other carriers may be applied directly to the lumen of the vagina. If the composition of the invention is in the form of a solution, an intravaginal tampon is soaked in the solution, then the tampon is placed inside the vagina.

For the composition and method of treatment according to the invention, the medicament is administered according to the following dosage. For the composition of this invention containing 8–14% (W/V) of saccharides as active ingredients, such composition is applied inside the vagina 1–3 times daily in doses of 3–5 ml, with the total sugar amount controlled to 0.24–2.1 grams daily dosage, generally applied before sleep at night or after arising in the morning, with an additional dose applied at noon for a few patients. For the patients suffering from severely abnormal vaginal bacterial flora and with the pH value of the vaginal secretion greater than 5.0, and if the vaginal Gram smear shows few or no Gram-positive bacilli, more extensive treatment is required with the sugar amount above 0.8 grams daily. For the patients having less severe disease with the pH value of vaginal secretion between 5.0 and 4.6, or if the vaginal Gram smear reveals Gram-positive bacilli, but in lesser abundance than that of any of Gram-negative bacilli, Gram-negative cocci, or Gram-positive cocci, a smaller dosage is used and the total sugar amount is limited to 0.8 grams or less.

During treatment with this composition, clinical symptoms may be observed daily and the vaginal pH value checked for change. Moreover, the vaginal Gram smear may be performed in order to check the change of bacterial flora and adjust the treatment accordingly if necessary. Generally, the composition of this invention can produce remarkable therapeutic effects 1–3 days after beginning of use, with symptoms improved significantly even disappearing, and pH values in the vagina reduced to normal levels and the Gram-positive bacilli in the vagina restored to dominance in the vaginal bacterial flora, at which time therapy with the composition should be stopped or the dosage be reduced, or the treatment continued at a low maintenance dosage.

For the method of this invention, the patients are provided with the composition containing only the saccharides of this invention as active ingredients, or the composition containing the saccharides, anti-fungal agent and/or anti-bacterial agent. Alternatively, the composition containing the saccharides of this invention as its active ingredients is administered in conjunction with suitable anti-fungal agent or anti-bacterial agent. For the latter case, the composition of this invention can be administered simultaneously with the anti-fungal and/or anti-bacterial agent or before/after the administration of the anti-fungal and/or anti-bacterial agent.

After the administration of this composition, the clinical symptoms of patients can be alleviated quickly, the numbers of Gram-positive bacilli are increased in the vagina, vaginal acidity is raised with the pH value reduced to 4.0–4.6, while the Gram-negative bacilli, Gram-negative cocci and other harmful abnormal bacteria are reduced substantially or even disappear. The composition of this invention is easy to prepare and to use with reliable effects.

EXPERIMENT EXAMPLE 1

Experiment in vitro with the composition of this invention: The effect of the composition in promoting the growth of Gram-positive bacilli and the production of acids.
Method:
(1) The preparation of the compositions: glucose and starch were used respectively to prepare the following compositions according to the method mentioned above:
   A. glucose 5.0%( W/V), yeast extract 1.0%( W/V), xanthan gum 1.6%(W/V), pH 5.0;
   B. starch 10.0 (W/V), yeast extract 1.0%( W/V), pH 5.0
   The compositions prepared above were filled into the tubes after sterilization, with each tube containing 5 ml, and pre-reduced for use.
(1) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension got ready. The vaginal Gram smear showed few Gram-positive bacilli but an abundance of Gram-negative bacilli, negative cocci and positive cocci.
(2) The above-mentioned specimen suspension was inoculated immediately into the tubes containing the above-mentioned compositions, 10 microliter for each tube, mixed homogeneously. Then the tubes were placed in the incubator for cultivation, at 37° C., anaerobically. Then, culture samples were taken from the tubes after 10 hours and 24 hours' culture respectively. The Gram smears of the samples were observed and the pH values of the samples were tested.
Results:
As shown in Table 1, although the Gram smear of the specimen showed few Gram-positive bacilli, the Gram positive bacilli grew remarkably in the compositions of this invention after specimen suspension inoculated and cultivated. Meanwhile the pH value of the compositions decreased.

TABLE 1

The Effect of the Compositions of this Invention in Promoting the Growth of Gram-positive Bacilli and the Production of Acids

| Saccharide contained in composition | Bacteria in specimen suspension | pH of the composition | 10 hours-culture | | 24 hours-culture | |
|---|---|---|---|---|---|---|
| | | | Bacteria | pH | Bacteria | pH |
| Glucose | G + b*, −** | 5.0 | G + b, +++ | 4.8 | G + b, ++++ | 4.2 |
| | G − b, ++++ | | G − b, ++ | | G − b, ++ | |
| | G − c, +++ | | G − c, − | | G − c, + | |
| | G + C, ++ | | G + c, + | | G + C, ++ | |
| Starch | G + b, − | 5.0 | G + b, ++ | 5.0 | G + b, ++++ | 4.0 |
| | G − b, ++++ | | G − b, ++ | | G − b, + | |
| | G − c, +++ | | G − c, + | | G − c, − | |
| | G + c, ++ | | G + c, ++ | | G + c, + | |

*G + b: Gram-positive bacilli, G − b: Gram-negative bacilli; G + c: Gram-positive cocci, G − c: Gram-negative cocci.
**
−No or less than one bacterium per field of vision under oil-immersion lens;
+: 1–9 bacteria per field of vision under oil-immersion lens;
++: About 10–99 bacteria per field of vision under oil-immersion lens;
+++: About 100 bacteria or more per field vision under oil-immersion lens, even uncountable;
++++: Bacteria clumped or aggregated.

Conclusion

The compositions of this invention have the effects in promoting the growth of Gram-positive bacilli and the production of the acids.

EXPERIMENT EXAMPLE 2

Experiment in vitro with the compositions of this invention: the effects of the compositions of the present invention in promoting the growth of Gram-positive bacilli and the production of acids.

Method:

(1) The preparation of the compositions: Different saccharides were used respectively to prepare the following compositions according to the method described above: glucose, fructose, galactose, mannose, lactose, lactulose, mycose, cellobiose, melibiose, melitose, maltooligosaccharide, isomaltooligosaccharide and fructooligosaccharide, dextrin, starch, and glycogen:

A. 5% glucose, 1.0% yeast extract, 1.6% xanthan gum, pH adjusted to 6.2;
B. 5% fructose, 1.0% yeast extract, 1.6% xanthan gum, pH adjusted to 6.2;
C. 5% galactose, 1.0% yeast extract, 1.6% xanthan gum, pH adjusted to 6.2;
D. 5% mannose, 1.0% yeast extract, 1.6% xanthan gum, pH adjusted to 6.2;
E. 10.0% lactose, 1.0% yeast extract, 1.6% xanthan gum, pH adjusted to 6.2;
F. 10.0% lactulose, 1.0% yeast extract, 1.6% xanthan gum, pH adjusted to 6.2;
G. 10.0% cellobiose, 1.0% yeast extract, 1.6% xanthan gum, pH adjusted to 6.2;
H. 10.0% mycose, 1.0% yeast extract, 1.6% xanthan gum, pH adjusted to 6.2;
I. 10.0% melibiose, 1.0% yeast extract, 1.6% xanthan gum, pH adjusted to 6.2;
J. 10.0% melitose, 1.0% yeast extract, 1.6% xanthan gum, pH adjusted to 6.2;
K. 10.0% maltooligosaccharide, 1.0% yeast extract, 1.6% xanthan gum, pH adjusted to 6.2;
L. 10.0% isomaltooligosaccharide, 1.0% yeast extract, 1.6% xanthan gum, pH adjusted to 6.2;
M. 10.0% fructooligosaccharide, 1.0% yeast extract, 1.6% xanthan gum, pH adjusted to 6.2;
N. 10.0% dextrin, 1.0% yeast extract, 0.5% xanthan gum, pH adjusted to 6.2;
O. 10.0% starch, 1.0% yeast extract, pH adjusted to 6.2;
P. 10.0% glycogen, 1.0% yeast extract, 1.6% xanthan gum, pH adjusted to 6.2;

(1) The preparation of the test tubes: Aforesaid compositions were filled into the test tubes, with each tube containing 5 ml, sterilized, and got ready for experiment.
(2) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension got ready. The vaginal Gram smear showed few Gram-positive bacilli but an abundance of Gram-negative bacilli, negative cocci and positive cocci.
(3) The above-mentioned specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, samples were taken respectively from each of the tubes. Then the Gram smears of the samples were observed and the pH values of culture samples were tested.

Results

As shown in Table 2, although there was few Gram positive bacilli in the vaginal secretion specimen, the Gram positive bacilli grew remarkably in the compositions containing separately different sugar of the present invention after the compositions were inoculated with specimen suspension and cultivated for 24 hours or 48 hours. Meanwhile the pH values in most of the composition tubes decreased to different levels. These results indicate that the compositions of the present invention containing 5% of hexose or containing 10% of ologosaccharides or polysaccharides exert effects in promoting the growth of Gram-positive bacilli.

TABLE 2

The Selective Effects of the Compositions of the Present Invention on Gram-positive Bacilli Growth and Acids-producing

| Saccharide contained in composition | Bacteria in specimen suspension | pH of the composition | 10 hours-culture | | 24 hours-culture | |
|---|---|---|---|---|---|---|
| | | | Bacteria | pH | Bacteria | pH |
| Glucose | G + b, − | 6.2 | G + b, ++ | 6.4 | G + b, +++ | 6.2 |
| | G − b, ++++ | | G − b, + | | G − b, + | |
| | G − c, +++ | | G − c, − | | G − c, − | |
| | G + c, ++ | | G + c, − | | C + c, ++ | |
| Fructose | G + b, − | 6.2 | G + b, ++ | 5.4–5.8 | G + b, +++ | 5.4–5.8 |
| | G − b, ++++ | | G − b, + | | G − b, + | |
| | G − c, +++ | | G − c, − | | G − c, − | |
| | G + c, ++ | | G + c, | | G + c, | |

TABLE 2-continued

The Selective Effects of the Compositions of the Present Invention on Gram-positive Bacilli Growth and Acids-producing

| Sacchride contained in composition | Bacteria in specimen suspension | pH of the composition | 10 hours-culture Bacteria | pH | 24 hours-culture Bacteria | pH |
|---|---|---|---|---|---|---|
| Galactose | G + b, − | 6.2 | G + b, ++ | 6.7 | G + b, + | 6.7 |
|  | G − b, ++++ |  | G − b, − |  | G − b, + |  |
|  | G + c, ++ |  | G − c, − |  | G − c, − |  |
|  | G + c, ++ |  | G + c, ++ |  | G + c, ++ |  |
| Mannose |  |  | G + b, ++ | 6.4 | G + b, +++ | 5.8 |
|  |  |  | G − b, + |  | G − b, + |  |
|  |  |  | G − c, − |  | G − c, − |  |
|  |  |  | G + c, ++ |  | G + c, + |  |
| Lactose | G + b, − | 6.2 | G + b, ++ | 5.8 | G + b, ++ | 5.1–5.4 |
|  | G − b, ++++ |  | G − b, + |  | G − b, + |  |
|  | G − c, +++ |  | G − c, − |  | G − c, − |  |
|  | G + c, ++ |  | G + c, +++ |  | G + c, + |  |
| Lactulose | G + b, − | 6.2 | G + b, +++ | 5.8–6.2 | G + b, + | 6.2 |
|  | G − b, ++++ |  | G − b, + |  | G − b, + |  |
|  | G − c, +++ |  | G − c, − |  | G − c, − |  |
|  | G + c, ++ |  | G + c, + |  | G + c, + |  |
| Cellobiose | G + b, − | 6.2 | G + b, ++ | 5.8 | G + b, ++ | 5.8 |
|  | G − b, ++++ |  | G − b, + |  | G − b, + |  |
|  | G − c, +++ |  | G − c, − |  | G − c, − |  |
|  | G + c, ++ |  | G + c, + |  | G + c, + |  |
| Mycose | G + b, − | 6.2 | G + b, ++ | 4.8 | G + b, +++ | 4.6–4.8 |
|  | G − b, ++++ |  | G − b, + |  | G − b, ++ |  |
|  | G − c, +++ |  | G − c, − |  | G − c, − |  |
|  | G + c, ++ |  | G + c, + |  | G + c, + |  |
| Melibiose | G + b, − | 6.2 | G + b, + | 6.2 | G + b, ++ | 5.8 |
|  | G − b, ++++ |  | G − b, ++ |  | G − b, ++ |  |
|  | G − c, +++ |  | G − c, + |  | G − c, − |  |
|  | G + c, ++ |  | G + c, + |  | G + c, + |  |
| Melitose | G + b, − | 6.2 | G + b, ++ | 6.7 | G + b, +++ | 5.8 |
|  | G − b, ++++ |  | G − b, + |  | G − b, ++ |  |
|  | G − c, +++ |  | G − c, + |  | G − c, − |  |
|  | G + c, ++ |  | G + c, + |  | G + c, + |  |
| Malto-oligo-Sacchride | G + b, − | 6.2 | G + b, ++ | 5.8 | G + b, +++ | 5.8 |
|  | G − b, ++++ |  | G − b, + |  | G − b, + |  |
|  | G − c, +++ |  | G − c, − |  | G − c, − |  |
|  | G + c, +++ |  | G + c, ++ |  | G + c, ++ |  |
| Fructo-oligo-saccharine | G + b, − | 6.2 | G + b, +++ | 5.8 | G + b, +++ | 6.2 |
|  | G − b, ++++ |  | G − b, ++ |  | G − b, + |  |
|  | G − c, +++ |  | G − c, − |  | G − c, − |  |
|  | G + c, ++ |  | G + c, + |  | G + c, − |  |
| Isomalto-oligo-Saccharide | G + b, − | 6.2 | G + b, ++ | 6.2 | G + b, +++ | 5.8 |
|  | G − b, ++++ |  | G − b, ++ |  | G − b, ++ |  |
|  | G − c, +++ |  | G − c, − |  | G − c, − |  |
|  | G + c, ++ |  | G + c, + |  | G + c, + |  |
| Dextrin | G + b, − | 6.2 | G + b, +++ | 6.2 | G + b, ++ | 5.8 |
|  | G − b, ++++ |  | G − b, ++ |  | G − b, + |  |
|  | G − c, +++ |  | G − c, − |  | G − c, − |  |
|  | G + c, ++ |  | G + c, + |  | G + c, − |  |
| Starch | G + b, − | 6.2 | G + b, ++ | 6.7 | G + b, ++ | 6.2 |
|  | G − b, ++++ |  | G − b, ++ |  | G − b, ++ |  |
|  | G − c, +++ |  | G − c, − |  | G − c, − |  |
|  | G + c, ++ |  | G + c, + |  | G + c, − |  |
| Glycogen | G + b, − | 6.2 | G + b, ++ | 6.4 | G + b, +++ | 6.2 |
|  | G − b, ++++ |  | G − b, ++ |  | G − b, ++ |  |
|  | G − c, +++ |  | G − c, − |  | G − c, − |  |
|  | G + c, ++ |  | G + c, + |  | G + c, + |  |

Conclusion

The compositions of the present invention containing saccharides as active ingredients have the effects in promoting the growth of Gram positive bacilli and producing acids.

EXPERIMENT EXAMPLE 3

Experiment in vitro with the compositions of this invention: The effects of the compositions of the present invention in promoting the growth of Gram-positive bacilli and producing acids.

Method:

(1) The preparation of the compositions: Different saccharides were used respectively to prepare the following compositions according to the method described above: glucose, fructose, galactose, mannose, lactose, lactulose, mycose, cellobiose, melibiose, melitose, malto-oligosaccharide, isomaltooligosaccharide and fructooligosaccharide, dextrin, starch, and glycogen:

A. 2.5% glucose, 1.0% yeast extract, 1.6% xanthan gum, pH adjusted to 6.2;

B. 2.5% fructose, 1.0% yeast extract, 1.6% xanthan gum, pH adjusted to 6.2;

C. 2.5% galactose, 1.0% yeast extract, 1.6% xanthan gum, pH adjusted to 6.2;

D. 2.5% mannose, 1.0% yeast extract, 1.6% xanthan gum, pH adjusted to 6.2;

E. 2.5% lactose, 1.0% yeast extract, 1.6% xanthan gum, pH adjusted to 6.2;

F. 2.5% lactulose, 1.0% yeast extract, 1.6% xanthan gum, pH adjusted to 6.2;

G. 2.5% cellobiose, 1.0% yeast extract, 1.6% xanthan gum, pH adjusted to 6.2;

H. 2.5% mycose, 1.0% yeast extract, 1.6% xanthan gum, pH adjusted to 6.2;

I. 2.5% melibiose, 1.0% yeast extract, 1.6% xanthan gum, pH adjusted to 6.2;

J. 2.5% melitose, 1.0% yeast extract, 1.6% xanthan gum, pH adjusted to 6.2;

K. 2.5% maltooligosaccharide, 1.0% yeast extract, 1.6% xanthan gum, pH adjusted to 6.2;

L. 2.5% isomaltooligosaccharide, 1.0% yeast extract, 1.6% xanthan gum, pH adjusted to 6.2;

M. 2.5% fructooligosaccharide, 1.0% yeast extract, 1.6% xanthan gum, pH adjusted to 6.2;

N. 2.5% dextrin, 1.0% yeast extract, 0.5% xanthan gum, pH adjusted to 6.2;

O. 2.5% starch, 1.0% yeast extract, pH adjusted to 6.2;

P. 2.5% glycogen, 1.0% yeast extract, 1.6% xanthan gum, pH adjusted to 6.2;

(1) The preparation of the test tubes: Aforesaid compositions were filled into the test tubes, with each tube containing 5 ml, sterilized, and got ready for experiment.

(2) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension got ready. The vaginal Gram smear showed few Gram-positive bacilli but an abundance of Gram-negative bacilli, negative cocci and positive cocci.

(3) The above-mentioned specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, samples were taken respectively from each of the tubes. Then the Gram smears of the samples were observed and the pH values of culture samples were tested.

Results

As shown in Table 3, although there was few Gram positive bacilli in the vaginal secretion specimen, the Gram positive bacilli grew in the compositions containing separately different sugar of the present invention after the compositions were inoculated with specimen suspension and cultivated for 24 hours or 48 hours. The results indicate that the compositions of the present invention containing 2.5% of saccharides exert effects in promoting the growth of Gram-positive bacilli.

TABLE 3

The Selective Effects of the Compositions of the Present Invention on Gram-positive Bacilli Growth and Acids-producing

| Sacchride contained in composition | Bacteria in specimen suspension | pH of the composition | 24 hours-culture Bacteria | pH | 48 hours-culture Bacteria | pH |
|---|---|---|---|---|---|---|
| Glucose | G + b, − | 6.2 | G + b, + | 5.4 | G + b, + | 4.4 |
|  | G − b, ++++ |  | G − b, ++ |  | G − b, +++ |  |
|  | G − c, +++ |  | G − c, − |  | G − c, − |  |
|  | G + c, ++ |  | G + c, − |  | C + c, + |  |
| Fructose | G + b, − | 6.2 | G + b, ++ | 5.4 | G + b, ++ | 6.4 |
|  | G − b, ++++ |  | G − b, ++ |  | G − b, +++ |  |
|  | G − c, +++ |  | G − c, − |  | G − c, − |  |
|  | G + c, ++ |  | G + c, − |  | G + c, − |  |
| Galactose | G + b, − | 6.2 | G + b, + | 6.7 | G + b, + | 4.8–5.1 |
|  | G − b, ++++ |  | G − b, ++ |  | G − b, +++ |  |
|  | G − c, +++ |  | G − c, − |  | G − c, − |  |
|  | G + c, ++ |  | G + c, − |  | G + c, − |  |
| Mannose | G + b, − | 6.2 | G + b, ++ | 5.4 | G + b, +++ | 6.2 |
|  | G − b, ++++ |  | G − b, + |  | G − b, + |  |
|  | G − c, +++ |  | G − c, − |  | G − c, − |  |
|  | G + c, ++ |  | G + c, + |  | G + c, − |  |
| Lactose | G + b, − | 6.2 | G + b, + | 7.0 | G + b, + | 6.7 |
|  | G − b, ++++ |  | G − b, − |  | G − b, ++ |  |
|  | G − c, +++ |  | G − c, − |  | G − c, − |  |
|  | G + c, ++ |  | G + c, + |  | G + c, ++ |  |
| Lactulose | G + b, − | 6.2 | G + b, + | 6.7 | G + b, + | 6.7 |
|  | G − b, ++++ |  | G − b, +++ |  | G − b, +++ |  |
|  | G − c, +++ |  | G − c, − |  | G − c, − |  |
|  | G + c, ++ |  | G + c, + |  | G + c, + |  |
| Cellobiose | G + b, − | 6.2 | G + b, + | 5.4 | G + b, ++ | 6.7 |
|  | G − b, ++++ |  | G − b, +++ |  | G − b, +++ |  |
|  | G − c, +++ |  | G − c, − |  | G − c, − |  |
|  | G + c, ++ |  | G + c, + |  | G + c, − |  |
| Mycose | G + b, − | 6.2 | G + b, ++ | 5.8 |  |  |
|  | G − b, ++++ |  | G − b, + |  |  |  |
|  | G − c, +++ |  | G − c, − |  |  |  |
|  | G + c, ++ |  | G + c, + |  |  |  |
| Melibiose | G + b, − | 6.2 | G + b, + | 6.4 |  |  |
|  | G − b, ++++ |  | G − b, +++ |  |  |  |
|  | G − c, +++ |  | G − c, − |  |  |  |
|  | G + c, ++ |  | G + c, + |  |  |  |
| Melitose | G + b, − | 6.2 | G + b, + | 7.0 |  |  |
|  | G − b, ++++ |  | G − b, ++ |  |  |  |
|  | G + c, +++ |  | G + c, − |  |  |  |
|  | G + c, ++ |  | G + c, ++ |  |  |  |
| Malto-oligo- | G + b, − | 6.2 | G + b, + | 6.4 |  |  |
|  | G − b, ++++ |  | G − b, +++ |  |  |  |

TABLE 3-continued

The Selective Effects of the Compositions of the Present Invention on Gram-positive Bacilli Growth and Acids-producing

| Sacchride contained in composition | Bacteria in specimen | pH of the composition | 24 hours-culture | | 48 hours-culture | |
|---|---|---|---|---|---|---|
| | | | Bacteria | pH | Bacteria | pH |
| Sacchride | G – c, +++ | | G – c, – | | | |
| | G + c, ++ | | G + c, + | | | |
| Fructo- | G + b, – | 6.2 | G + b, ++ | 6.7 | | |
| oligo- | G – b, ++++ | | G – c, ++ | | | |
| Saccharide | G – c, +++ | | G – c, – | | | |
| | G + c, ++ | | G + c, + | | | |
| Isomalto- | G + b, – | 6.2 | G + b, + | 6.4 | | |
| oligo | G – b, ++++ | | G – b, +++ | | | |
| Saccharide | G – c, +++ | | G – c, – | | | |
| | G + c, ++ | | G + c, + | | | |
| Dextrin | G + b, – | 6.2 | G + b, + | 6.4 | | |
| | G – b, ++++ | | G – b, ++ | | | |
| | G – c, +++ | | G – c, – | | | |
| | G + c, ++ | | G + c, + | | | |
| Starch | G + b, – | 6.2 | G + b, + | 7.0 | | |
| | G – b, ++++ | | G – b, +++ | | | |
| | G – c, +++ | | G – c, – | | | |
| | G + c, ++ | | G + c, + | | | |
| Glycogen | G + b, – | 6.2 | G + b, + | 6.4 | | |
| | G – b, ++++ | | G – b, ++ | | | |
| | G + c, +++ | | G + c, – | | | |
| | G + c, ++ | | G + c, ++ | | | |

Conclusion

The compositions of the present invention containing 2.5% of saccharide have the effects in promoting the growth of Gram positive bacilli.

EXPERIMENT EXAMPLE 4

Experiment in vitro with the compositions of this invention: effects of the compositions of this invention in promoting the growth of Gram-positive bacilli and the production of acids Method:

(1) The preparation of the compositions: Different saccharides were used respectively to prepare the following compositions according to the method described above: glucose, fructose, galactose, mannose, lactose, lactulose, mycose, cellobiose, melibiose, melitose, maltooligosaccharide, isomaltooligosaccharide and fructooligosaccharide, dextrin, starch, and glycogen:

A. 7.2% glucose, 1.0% yeast extract, 1.6% xanthan gum, pH adjusted to 6.2;
B. 7.2% fructose, 1.0% yeast extract, 1.6% xanthan gum, pH adjusted to 6.2;
C. 7.2% galactose, 1.0% yeast extract, 1.6% xanthan gum, pH adjusted to 6.2;
D. 7.2% mannose, 1.0% yeast extract, 1.6% xanthan gum, pH adjusted to 6.2;
E. 17% lactose, 1.0% yeast extract, 1.6% xanthan gum, pH adjusted to 6.2;
F. 17% lactulose, 1.0% yeast extract, 1.6% xanthan gum, pH adjusted to 6.2;
G. 17% cellobiose, 1.0% yeast extract, 1.6% xanthan gum, pH adjusted to 6.2;
H. 17% mycose, 1.0% yeast extract, 1.6% xanthan gum, pH adjusted to 6.2;
I. 17% melibiose, 1.0% yeast extract, 1.6% xanthan gum, pH adjusted to 6.2;
J. 17% melitose, 1.0% yeast extract, 1.6% xanthan gum, pH adjusted to 6.2;
K. 17% maltooligosaccharide, 1.0% yeast extract, 1.6% xanthan gum, pH adjusted to 6.2;
L. 17% isomaltooligosaccharide, 1.0% yeast extract, 1.6% xanthan gum, pH adjusted to 6.2;
M. 17% fructooligosaccharide, 1.0% yeast extract, 1.6% xanthan gum, pH adjusted to 6.2;
N. 17% dextrin, 1.0% yeast extract, 0.5% xanthan gum, pH adjusted to 6.2;
O. 17% starch, 1.0% yeast extract, pH adjusted to 6.2;
P. 17% glycogen, 1.0% yeast extract, 1.6% xanthan gum, pH adjusted to 6.2;

(1) The preparation of the test tubes: Aforesaid compositions were filled into the test tubes, with each tube containing 5 ml, sterilized, and got ready for experiment.

(2) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension got ready. The vaginal Gram smear showed few Gram-positive bacilli but an abundance of Gram-negative bacilli, negative cocci and positive cocci.

(3) The above-mentioned specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, samples were taken respectively from each of the tubes. Then the Gram smears of the samples were observed and the pH values of culture samples were tested.

Results

As shown in Table 4, although there was few Gram positive bacilli in the vaginal secretion specimen, the Gram positive bacilli grew remarkably in the compositions containing separately different sugar of the present invention after the compositions were inoculated with specimen suspension and cultivated for 24 hours or 48 hours. Meanwhile the pH values in most of the composition tubes decreased to different levels. The results indicate that the compositions of the present invention containing 7.2% of hexose or containing 17% of oligosaccharides or poloysaccharides exert effects in promoting the growth of Gram-positive bacilli.

TABLE 4

The Selective Effects of the Compositions of the Present Invention on Gram-positive Bacilli Growth and Acids-producing

| Sacchride contained in composition | Bacteria in specimen suspension | pH of the composition | 24 hours-culture | | 48 hours-culture | |
|---|---|---|---|---|---|---|
| | | | Bacteria | pH | Bacteria | pH |
| Glucose | G + b, – | 6.2 | G + b, ++ | 6.4 | G + b, ++ | 5.8 |
| | G – b, ++++ | | G – b, + | | G – b, ++ | |
| | G – c, +++ | | G – c, – | | G – c, – | |
| | G + c, ++ | | G + c, – | | C + c, ++ | |
| Fructose | G + b, – | 6.2 | G + b, ++ | 6.2 | G + b, ++ | 5.4 |
| | G – b, ++++ | | G – b, ++ | | G – b, + | |
| | G – c, +++ | | G – c, – | | G – c, – | |
| | G + c, ++ | | G + c, + | | G + c, + | |
| Galactose | G + b, – | 6.2 | G + b, ++ | 6.7 | G + b, ++ | 6.4 |
| | G – b, ++++ | | G – b, ++ | | G – b, ++ | |
| | G – c, +++ | | G – c, – | | G – c, – | |
| | G + c, ++ | | G + c, + | | G + c, ++ | |

TABLE 4-continued

The Selective Effects of the Compositions of the Present Invention on Gram-positive Bacilli Growth and Acids-producing

| Sacchride contained in composition | Bacteria in specimen | pH of the composition | 24 hours-culture Bacteria | pH | 48 hours-culture Bacteria | pH |
|---|---|---|---|---|---|---|
| Mannose | G + b, − | 6.2 | G + b, ++ | 6.4 | G + b, ++ | 5.8 |
| | G − b, ++++ | | G − b, + | | G − b, + | |
| | G − c, +++ | | G − c, − | | G − c, − | |
| | G + c, ++ | | G + c, + | | G + c, ++ | |
| Lactose | G + b,− | 6.2 | G + b, + | 5.8 | G + b, ++ | 6.2 |
| | G − b, ++++ | | G − b, + | | G − b, + | |
| | G − c, +++ | | G − c, − | | G − c, − | |
| | G + c, ++ | | G + c, + | | G + c, ++ | |
| Lactulose | G + b, − | 6.2 | G + b, + | 6.2 | | |
| | G − b, ++++ | | G − b, + | | | |
| | G − c, +++ | | G − c, − | | | |
| | G + c, ++ | | G + c, + | | | |
| Cellobiose | G + b, − | 6.2 | G + b, + | 5.8 | G + b, ++ | 6.2 |
| | G − b, ++++ | | G − b, ++ | | | |
| | G − c, +++ | | G − c, − | | | |
| | G + c, ++ | | G + c, + | | | |
| Mycose | G + b, − | 6.2 | G + b, + | 5.8 | | |
| | G − b, ++++ | | G − b, + | | | |
| | G − c, +++ | | G − c, − | | | |
| | G + c, ++ | | G + c, ++ | | | |
| Melibiose | G + b, − | 6.2 | G + b, + | 6.2 | | |
| | G − b, ++++ | | G − b, ++ | | | |
| | G − c, +++ | | G − c, − | | | |
| | G + c, ++ | | G + c, ++ | | | |
| Melitose | G + b, − | 6.2 | G + b, + | 6.7 | | |
| | G − b, ++++ | | G − b, ++ | | | |
| | G − c, +++ | | G − c, − | | | |
| | G + c, ++ | | G + c, ++ | | | |
| Malto-oligo-Sacchride | G + b, − | 6.2 | G + b, + | 6.4 | | |
| | G − b, ++++ | | G − b, + | | | |
| | G − c, +++ | | G − c, + | | | |
| | G + c, ++ | | G + c, + | | | |
| Fructo-oligo-Saccharide | G + b, − | 6.2 | G + b, + | 5.8 | | |
| | G − b, ++++ | | G − b, ++ | | | |
| | G − c, +++ | | G − c, − | | | |
| | G + c, ++ | | G + c, + | | | |
| Isomalto-oligo-Saccharide | G + b, − | 6.2 | G + b, + | 6.2 | | |
| | G − b, ++++ | | G − b, ++ | | | |
| | G − c, +++ | | G − c, − | | | |
| | G + c, ++ | | G + c, ++ | | | |
| Dextrin | G + b, − | 6.2 | G + b, + | 6.7 | | |
| | G − b, ++++ | | G − b, + | | | |
| | G − c, +++ | | G − c, − | | | |
| | G + c, ++ | | G + c, ++ | | | |
| Starch | G + b, − | 6.2 | G + b, + | 6.4 | | |
| | G − b, ++++ | | G − b, ++ | | | |
| | G − c, +++ | | G − c, − | | | |
| | G + c, ++ | | G + c, ++ | | | |
| Glycogen | G + b, − | 6.2 | G + b, + | 6.2 | | |
| | G − b, ++++ | | G − b, ++ | | | |
| | G − c, +++ | | G − c, − | | | |
| | G + c, ++ | | G + c, + | | | |

Conclusion

The compositions of the present invention containing 7.2% of hexose or containing 17% of oligosaccharides or polysaccharides exert effects in promoting the growth of Gram-positive bacilli.

EXPERIMENT EXAMPLE 5

Case Report 1

Ms. Li, aged 51. She had suffered discomfort and hurting in vulva repeatedly after the menopause for more than one year and vaginitis was once diagnosed in the hospital. But the treatments with several kinds of antibiotics as well as vaginal douches had little effects in relieving the symptoms. The present inventor took the vaginal swabs from the patient and tested the vaginal secretions. The pH value of the vaginal swab was 5.4 and the Gram smear showed a lot of medium and bottom layer mucosal cells, a few of white blood cells, a small amount of Gram positive cocci, a few of Gram negative bacilli, but no Gram positive bacilli was found. Thus senile vaginitis and the disturbance of vaginal bacterial flora were diagnosed. Cotton balls soaked in the solution of the present invention was placed inside vagina, one ball for each time, once a day, generally before sleep at night and took out the next morning. Each cotton ball contained about 5 ml of the solution containing 12% of lactose, with the pH value 4.0. After successive treatment for four days, the pH value of the vaginal swab changed to 4.4 and the vaginal Gram smear showed Gram positive cocci, no Gram positive bacilli was found. Then the cotton balls having soaked in the solution containing 12% of lactose with the pH value 5.1 was administered just in the same way. Two days later, the pH value of the vaginal swab was 4.6 and the vaginal Gram smear showed some big Gram positive bacilli in Y/V shapes or in Y/V arrangements. The treatment was continued for another two days and the pH value of the vaginal swab decreased to 4.0 and the majority of the bacteria were Gram positive bacilli, and there were few Gram positive cocci. The patient's symptoms disappeared.

EXPERIMENT EXAMPLE 6

Case Report 2

Ms. Jiang, female, aged 30. The vaginal secretions of hers had exhibited unpleasant fish-odor, accompanying pruritus of vulvae for 2 years. After having born a child two years ago this patient had begun suffering from the increased quantity of vaginal secretions, which had exhibited unpleasant fish-odor especially after intercourse, and from pruritus of the vulvae which was so severe sometimes that she could not fall asleep. Having been tested and reported "neuplasma positive" in one hospital, she had been treated with several antibiotics which could relieve her symptoms temporarily. But the symptoms usually relapsed after the menstruation. She had also used various vaginal douches, and the symptoms relieved temporarily and then relapsed after stopping treatments. The present inventor found that there were a great mass of bacteria in Gram smears of the vaginal secretions of the patient and most of them were Gram negative bacilli and Gram negative cocci, there was few Gram positive bacilli and a few of white blood cells. The pH values of the vaginal secretions of this patient was 5.4. Diagnosed as "bacterial vaginosis" by the present inventor, this patient was treated with the composition of this invention, which contained 12% (W/V) of lactose and the pH value was 5.0. The drug was intravaginally administered, 3 ml for each time, once a day. After the treatment continued successively for three days, the symptoms of the patient relieved significantly and the pH value of the vaginal secretions decreased to 4.6. The Gram smears showed a lot of Gram-negative bacilli, Gram negative cocci, but the quantity of Gram positive cocci increased and many of Gram positive bacilli appeared.

Advantages Compared to Anti-bacterial Treatment

Anti-bacterial drugs, based on the views of etiology, control the abnormal bacteria that grow excessively and cause pathological reaction by killing or suppressing such bacteria. This method has the following shortcomings: (1) After repeated treatments with antibacterial drugs, the bacteria may gain drug-resistances and it may lead to the failure of the antibacterial therapy. (2) Anti-bacterial treatment may results in the superinfection by drug-resistant bacteria. (3) Anti-bacterial drugs may be allergic to human body and may have other kinds of adverse effects to skin or vaginal mucous membrane. Compositions containing lactic acid or acetic acid or other selective bacterial inhibitors as its active ingredients, for example, the compositions described in the patent applications of GB2112285A and EP-A-0257007, exert strong prohibiting effects on the pathogens and have no remarkable prohibiting effects on lactobacilli. Thus they may exert indirectly the favorable effects on the growth of lactobacilli in the vagina. The compositions themselves, however, cannot directly and remarkably promote the growth of lactobacilli in the vagina. The effects of these compositions in increasing the acidity in the vagina last only for a short period of time, and it is very hard for the physiological Gram-positive bacilli to restore and dominate over the vaginal bacterial flora.

The compositions of this invention can stimulate the growth of Gram-positive bacilli and increase acidity in the vagina, and thus suppress Gram-negative bacilli, Gram negative cocci, and Gram-positive cocci thereby. Seen from above analysis, the technologies and compositions of this invention actually enhance the natural physiological anti-disease mechanisms in the vagina and fundamentally avoid and overcome the disadvantages of the disturbance of vaginal bacterial flora by anti-bacterial treatment, therefore have remarkable advantages.

Advantages Compared to Lactobacilli Preparations

Firstly, the effects of lactobacilli preparations in the treatment of severe disturbance of the vaginal bacterial flora, such as typical bacterial vaginosis, are often variable. Secondly, the lactobacilli preparations are more difficult to produce and store and the production cost is higher. The compositions of this invention has a lower cost of production and longer effective period, and is significantly superior over the lactobacilli preparations. Moreover, the compositions of this invention improve the condition of the local micro-habitat in the vagina, thus promote the growth of the endogenous Gram positive bacilli in the vagina. It should be better than the direct supplement of the exogenous lactobacilli strains.

COMPOSITION EXAMPLES

Example 1

2.5 g fructose and 1.6 g xanthan gum were mixed homogeneously, and then some distilled water is added to the resulting misture while stirring in order to dissolve the sugar component and swell xanthan gum to homogeneous viscous gel. A suitable amount of lactic acid is added to adjust the pH of the solution to 4.1. Distilled water was added to make the total volume of the solution equal to 100 ml. The resulting solution was sterilized by means of intermittent sterilization.

Example 2

100 ml of the composition in the following formulation was prepared substantially according to the method as described in Example 1, except that the pH value was adjusted with 0.5 N sodium hydroxide.

| | |
|---|---|
| Maltooligosaccharide | 17.0% (W/V) |
| Yeast extract | 1.0% (W/V) |
| Xanthan gum | 1.4% (W/V) |
| Distilled water | q.s. |
| pH | 5.4 |

Example 3

100 ml of the composition in the following formulation was prepared substantially according to the method as described in Example 1.

| | |
|---|---|
| Maltooligosaccharide | 2.5% (W/V) |
| Xanthan gum | 1.6% (W/V) |
| Distilled water | q.s. |
| pH | 4.8 |

Example 4

100 ml of the composition in the following formulation was prepared substantially according to the method as described in Example 1.

| | |
|---|---|
| Maltooligosaccharide | 10.0% (W/V) |
| Yeast extract | 1.0% (W/V) |
| Xanthan gum | 1.6% (W/V) |
| Distilled water | q.s. |
| pH | 5.4 |

Example 5

100 ml of the composition in the following formulation was prepared substantially according to the method as described in Example 1.

| | |
|---|---|
| Fructose | 7.2% (W/V) |
| Xanthan gum | 1.6% (W/V) |
| Yeast extract | 0.8% (W/V) |
| Distilled water | q.s. |
| pH | 4.8 |

Example 6

100 ml of the composition in the following formulation was prepared substantially according to the method as described in Example 1.

| | |
|---|---|
| Fructooligosaccharide | 14.0% (W/V) |
| Histidine | 100 ppm |
| Methionine | 50.0 ppm |
| Riboflavin | 0.2 ppm |
| Thiamine | 0.2 ppm |
| Nicotinic acid | 0.2 ppm |
| Calcium pantothenate | 0.2 ppm |
| Xanthan gum | 1.8% (W/V) |
| Distilled water | q.s. |
| pH | 5.5 |

Example 7

100 ml of the composition in the following formulation was prepared according to the following method. The following ingredients were mixed, heated and stirred until the mixture became a paste. The pH value was adjusted with sodium hydroxide solution to 7.0. Then the mixture was sterilized.

| | |
|---|---|
| Amylopectin | 10.0% (W/V) |
| Mannose | 2.0% (W/V) |
| Yeast extract | 1.0% (W/V) |
| Distilled water | q.s. |
| pH | 5.4 |

Example 8

100 ml of the composition in the following formulation was prepared substantially according to the method as described in Example 1.

| | |
|---|---|
| Dextrin | 10.0% (W/V) |
| Glucose | 2.0% (W/V) |
| Histidine | 100 ppm |
| Methionine | 50.0 ppm |
| Riboflavin | 0.2 ppm |
| Thiamine | 0.2 ppm |
| Nicotinic acid | 0.2 ppm |
| Calcium pantothenate | 0.2 ppm |
| Xanthan gum | 1.0% (W/V) |
| pH | 6.0 |

The compositions of this invention are simply and can be easily manufactured at low cost.

What is claimed is:

1. A method of treating vaginitis and a disturbance of vaginal bacterial flora, accompanied with reduction of the number of Gram-positive bacilli, comprising vaginal administration to a subject in need of such treatment a therapeutically effective amount of the following composition comprising;

(a) 2.5% to 17% (W/V), based on total volume of the composition, of starch,
   (b) a sufficient amount of a pharmaceutically acceptable acid or alkali which results in a pH of the composition from about 4.1 to about 7.2.

2. The method according to claim 1, wherein the composition further comprises a pharmaceutically acceptable viscous base.

3. The method according to claim 1, wherein the disturbance of vaginal bacterial flora is bacterial vaginosis.

4. The method according to claim 2, wherein the viscous base comprises from about 1.0 to about 2.2% (W/V) xanthan gum.

5. The method according to claim 1, wherein the composition further comprises an effective amount of an anti-fungal agent.

6. The method according to claim 5, wherein the anti-fungal agent is selected from ketoconazole, terconazole itraconazole and fluconazole.

7. The method according to claim 1, further comprising an effective amount of an anti-bacterial agent that selectively inhibits Gram-negative bacilli.

8. The method according to claim 7, wherein the anti-bacterial agent is metronidazole, polymyxin, or aztreonam.

\* \* \* \* \*